(12) United States Patent
Henderson et al.

(10) Patent No.: US 7,060,448 B2
(45) Date of Patent: Jun. 13, 2006

(54) EVALUATING BINDING AFFINITIES BY FORCE STRATIFICATION AND FORCE PANNING

(75) Inventors: Eric Henderson, Ames, IA (US); Curtis Mosher, Ames, IA (US)

(73) Assignee: BioForce Nanosciences, Inc., Ames, IA (US)

( * ) Notice: Subject to any disclaimer, the term of this patent is extended or adjusted under 35 U.S.C. 154(b) by 0 days.

(21) Appl. No.: 10/958,092

(22) Filed: Oct. 4, 2004

(65) Prior Publication Data

US 2005/0059091 A1    Mar. 17, 2005

Related U.S. Application Data

(63) Continuation of application No. 09/974,757, filed on Oct. 9, 2001, now abandoned.

(60) Provisional application No. 60/238,566, filed on Oct. 10, 2000.

(51) Int. Cl.
*G01N 33/53* (2006.01)

(52) U.S. Cl. .............. 435/7.1; 435/4; 435/6; 435/7.2; 435/287.1; 435/287.2; 435/287.9; 436/517; 436/518; 436/524; 436/807; 73/104; 73/105; 356/501

(58) Field of Classification Search ............ 435/4, 435/7.1–7.2, 287.1, 287.2, 287.9; 436/517–518, 436/524, 807; 422/55, 266, 50, 57, 68.1, 422/99; 73/104–105; 250/307; 356/501
See application file for complete search history.

(56) References Cited

U.S. PATENT DOCUMENTS

| | | | |
|---|---|---|---|
| 4,728,591 A | 3/1988 | Clark et al. | |
| 5,106,729 A | 4/1992 | Lindsay et al. | |
| 5,138,174 A | 8/1992 | Tang | |
| 5,143,854 A | 9/1992 | Pirrung et al. | |
| 5,314,829 A | 5/1994 | Coles | |
| 5,346,683 A | 9/1994 | Green et al. | |
| 5,363,697 A | 11/1994 | Nakagawa | |
| 5,372,930 A | 12/1994 | Colton et al. | |
| 5,384,261 A | 1/1995 | Winkler et al. | |
| 5,440,122 A | 8/1995 | Yasutake | |
| 5,443,791 A | 8/1995 | Cathcart et al. | |
| 5,445,934 A | 8/1995 | Fodor et al. | |

(Continued)

FOREIGN PATENT DOCUMENTS

JP         06124680         5/1994

(Continued)

OTHER PUBLICATIONS

Lee et al. Sensing discrete streptavidin-biotin interactions with atomic force microscopy. Langmuir (1994), vol. 10, pp. 354-357.*

(Continued)

*Primary Examiner*—Long V. Le
*Assistant Examiner*—Leon Y. Lum
(74) *Attorney, Agent, or Firm*—Michael Best & Friedrich LLP

(57) ABSTRACT

The present invention is a method for selectively removing objects from a surface utilizing a probe. The probe is scanned over the surface utilizing a greater and greater relative amount of force so that a certain number of the objects are removed from the surface. The force required to remove the objects from the surface can be calculated utilizing Hook's law and the spring constant of the probe. After removal of the objects that have a relatively weaker binding affinity with the surface, the remaining objects can be harvested, characterized, and subjected to further study.

14 Claims, 5 Drawing Sheets

U.S. PATENT DOCUMENTS

| | | | |
|---|---|---|---|
| 5,445,971 A | 8/1995 | Rohr | |
| 5,453,970 A | 9/1995 | Rust et al. | |
| 5,467,642 A | 11/1995 | Hosaka et al. | |
| 5,472,881 A | 12/1995 | Beebe et al. | |
| 5,482,601 A | 1/1996 | Ohshima et al. | |
| 5,514,540 A | 5/1996 | Teoule et al. | |
| 5,514,550 A | 5/1996 | Findlay et al. | |
| 5,519,212 A | 5/1996 | Elings et al. | |
| 5,532,128 A | 7/1996 | Eggers et al. | |
| 5,571,639 A | 11/1996 | Hubbell et al. | |
| 5,601,982 A | 2/1997 | Sargent et al. | |
| 5,604,097 A | 2/1997 | Brenner | |
| 5,620,854 A | 4/1997 | Holzrichter et al. | |
| 5,666,190 A | 9/1997 | Quate et al. | |
| 5,670,322 A | 9/1997 | Eggers et al. | |
| 5,688,486 A | 11/1997 | Watson et al. | |
| 5,720,928 A | 2/1998 | Schwartz | |
| 5,744,305 A | 4/1998 | Fodor et al. | |
| 5,753,088 A | 5/1998 | Olk | |
| 5,760,300 A | 6/1998 | Kajimura | |
| 5,763,768 A | 6/1998 | Henderson et al. | |
| 5,789,167 A | 8/1998 | Konrad | |
| 5,800,992 A | 9/1998 | Fodor et al. | |
| 5,837,832 A | 11/1998 | Chee et al. | |
| 5,840,862 A | 11/1998 | Bensimon et al. | |
| 5,846,724 A | 12/1998 | Bensimon et al. | |
| 5,851,769 A | 12/1998 | Gray et al. | |
| 5,866,328 A | 2/1999 | Bensimon et al. | |
| 5,866,434 A | 2/1999 | Massey et al. | |
| 5,874,219 A | 2/1999 | Rava et al. | |
| 5,874,668 A * | 2/1999 | Xu et al. | 73/105 |
| 5,958,701 A | 9/1999 | Green et al. | |
| 5,965,133 A | 10/1999 | Cantor et al. | |
| 5,981,733 A | 11/1999 | Gamble et al. | |
| 5,985,356 A | 11/1999 | Schultz et al. | |
| 5,992,226 A | 11/1999 | Green et al. | |
| 5,993,627 A | 11/1999 | Anderson et al. | |
| 6,004,617 A | 12/1999 | Schultz et al. | |
| 6,024,925 A | 2/2000 | Little et al. | |
| 6,033,911 A | 3/2000 | Schultz et al. | |
| 6,045,671 A | 4/2000 | Wu et al. | |
| 6,080,586 A | 6/2000 | Baldeschwieler et al. | |
| 6,083,763 A | 7/2000 | Balch | |
| 6,087,274 A | 7/2000 | Tonucci et al. | |
| 6,110,426 A | 8/2000 | Shalon et al. | |
| 6,123,819 A | 9/2000 | Peeters | |
| 6,143,574 A | 11/2000 | Karlsson et al. | |
| 6,146,899 A | 11/2000 | Porter et al. | |
| 6,159,742 A | 12/2000 | Lieber et al. | |
| 6,171,797 B1 | 1/2001 | Perbost | |
| 6,180,114 B1 | 1/2001 | Yager | |
| 6,200,737 B1 | 3/2001 | Walt et al. | |
| 6,203,814 B1 | 3/2001 | Fisher et al. | |
| 6,214,552 B1 | 4/2001 | Heroux et al. | |
| 6,218,122 B1 | 4/2001 | Friend et al. | |
| 6,231,744 B1 | 5/2001 | Ying et al. | |
| 6,232,706 B1 | 5/2001 | Dai et al. | |
| 6,239,273 B1 | 5/2001 | Pease et al. | |
| 6,255,469 B1 | 7/2001 | Seeman et al. | |
| 6,270,946 B1 | 8/2001 | Miller | |
| 6,278,231 B1 | 8/2001 | Iwasaki et al. | |
| 6,284,497 B1 | 9/2001 | Sabanayagam et al. | |
| 6,287,850 B1 | 9/2001 | Besemer et al. | |
| 6,289,717 B1 | 9/2001 | Thundat et al. | |
| 6,309,831 B1 | 10/2001 | Goldberg et al. | |
| 6,329,209 B1 | 12/2001 | Wagner et al. | |
| 6,331,396 B1 | 12/2001 | Silverman | |
| 6,350,609 B1 | 2/2002 | Morozov et al. | |
| 6,395,554 B1 | 5/2002 | Regan et al. | |
| 6,406,921 B1 | 6/2002 | Wagner et al. | |
| 6,416,952 B1 | 7/2002 | Pirrung et al. | |
| 6,420,105 B1 | 7/2002 | Landfield et al. | |
| 6,436,647 B1 | 8/2002 | Quate et al. | |
| 6,518,168 B1 | 2/2003 | Clem et al. | |
| 6,573,369 B1 | 6/2003 | Henderson et al. | |
| 2002/0042081 A1 | 4/2002 | Henderson et al. | |
| 2002/0063212 A1 | 5/2002 | Mirkin et al. | |
| 2002/0076927 A1 | 6/2002 | Henderson et al. | |
| 2002/0114987 A1 | 8/2002 | Oscarsson et al. | |
| 2002/0122873 A1 | 9/2002 | Mirkin et al. | |
| 2002/0123135 A1 | 9/2002 | Henderson et al. | |
| 2002/0146714 A1 | 10/2002 | Lieber et al. | |
| 2002/0172943 A1 | 11/2002 | Henderson et al. | |
| 2002/0179434 A1 | 12/2002 | Dai et al. | |
| 2003/0013111 A1 | 1/2003 | Henderson et al. | |

FOREIGN PATENT DOCUMENTS

| | | |
|---|---|---|
| JP | 07027771 | 1/1995 |
| JP | 08094646 | 4/1996 |
| WO | WO 92/15709 | 9/1992 |
| WO | WO 96/31775 | 10/1996 |
| WO | WO 97/06420 | 2/1997 |
| WO | WO 97/18326 | 5/1997 |
| WO | WO 98/05920 | 2/1998 |
| WO | WO 98/18959 | 5/1998 |
| WO | WO 99/31267 | 6/1999 |
| WO | WO 00/04382 | 1/2000 |
| WO | WO 00/04389 | 1/2000 |
| WO | WO 00/04390 | 1/2000 |
| WO | WO 00/36136 | 6/2000 |
| WO | WO 00/41213 | 7/2000 |
| WO | WO 00/46406 | 8/2000 |
| WO | WO 01/60316 | 8/2001 |
| WO | WO 01/918555 | 12/2001 |
| WO | WO 03/001633 | 1/2003 |
| WO | WO 03/036767 | 5/2003 |
| WO | WO 03/038033 | 5/2003 |
| WO | WO 03/048314 | 6/2003 |
| WO | WO 03/052514 | 6/2003 |

OTHER PUBLICATIONS

Baselt, D.R., et al., "A biosensor based on magnetoresistance technology" *Biosens. Bioelectorn,* 1998, 13(7-8):731-739.

Florin, E., et al., "Adhesion forces between individual ligan-receptor pairs" *Science,* 1994, 264:415-417.

Mazzola, L., "Imaging biomolecule arrays by atomic force microscopy" *Biophysical Journal,* 1995, 68:1653-1660.

Allen, et al. "Detection of Antigen-Antibody Binding Events with the Atomic Force Microscope" *Biochemistry,* (1997) 36:7457-7464.

"Microbeam Mass Spectrometry" *Chemical Science and Technology Laboratory, Surface and Microanalysis Science Division* http://www.cstl.nist.gov/div837/Divisoin/expertise/ions/masspec1.htm Jul. 18, 2002.

Abstracts of Papers Part 1, 214th "Abstract 027" *ACS National Meeting American Chemical Society,* Sep. 1997, 2 pgs.

Allison, D., et al., "Direct atomic force microscopy imaging of *Eco*RI endonuclease site specifically bound to plasmid DNA molecules" *PNAS USA,* 1996, 93:8826-8829.

Allison, D., et al., "Mapping Individual Cosmid DNAs by Direct AFM Imaging" *Genomics,* 1997, 41:379-384.

Alves, et al., Atomic scale imaging of alkanethiolate monolayers at gold surfaces with atomic force microscopy: *J. Am. Chem. Soc.,* Feb. 1992,114(4):1222-1227.

Amro, et al., "Patterning surfaces using tip-directed displacement and self-assembly" *Langmuir,* 2000, 16:3006-3009.

Anwander, et al., "Surface characterization and functionalization of MCM-41 silicas via silazane silylation" *J. Phys. Chem. B.,* 2000, 104:3532-3544.

Arntz, et al., "Label-free protein assay based on a nanomechanical cantilever array" *Nanotechnology,* 14 (2003) 86-90.

Ausubel, F.M., et al. "Current Protocols in Molecular Biology" 1993 ed. vol. 1&2, 1993, Green Publishing Associates and Wiley-Interscience.

Avouris, P., et al., "Engineering Carbon Nanotube and Nanotubes Circuits Using Electrical Breakdown" *Science,* Apr. 2001, 292(5517):706-799.

Bailey, C.P., et al., "Cationic oligonucleotides can mediate specific inhibition of gene expression in Xenopus oocytes" *Nuc. Acids Res.,* 1998, 26(21):4860-4867.

Bain, et al., "Modeling organic surfaces with self-assembled monolayers" *Agnew. Chem. Int. Ed. Engl.,* 1989, 28(4):506-512.

Bedouelle, H., "Reagentless fluorescent Immunosensors" *Antibody Engineering,* IBC's 13th International Conference, Dec. 2, 2002.

Belaubre, P. et al., "Fabrication of biological microarrays using microcantilevers" *Applied Physics Letters,.* May 5, 2003, 82(18):3122-3124.

Bensimon, A., et al., "Alignment and sensitive detection of DNA by a moving interface" *Science,* Sep. 30, 1994; 265(5181):2096-2098 [PMID 7522347] Abstract.

Berggren, et al., "Microlithography by using neutral metastable atoms and self-assembled monolayers" *Science,* Sep. 1995, 269(5228):1255-1257.

Bernard, et al. "Printing patterns of proteins" *Langmuir The ACS Journal of Surfaces and Colliod,* Apr. 1998, 14(9):2225-2229.

Binggeli, et al., "Influence of capillary condensation of water on nanotribology studied by force microscopy" *Appl. Phys. Lett.,* Jul. 1994, 65(4):415-417.

Binning, et al., "Surface studies by scanning tunneling microscopy" *Phys. Rev. Lett.,* 1982, 49(1):57-61.

Binning, G., et al., Atomic force microscope *Phys. Rev. Lett.,* 1986, 56(9):930-933.

Bishop, et al., "Self-assembled monolayers: recent developments and applications" *Colloid & Interface Science,* Feb. 1996, 1:127-136.

Bottomley, L., "Scanning probe microscopy" *Anal. Chem.,* Jun. 1998, 70(12):425R-475R.

Brandow, S., et al., "Metal pattern fabrication using the local electric field of conducting atomic force microscope probe" *J. Vac. Sci. Technol.,* May/Jun. 1997, 15(3):1455-1459.

Brenner, S., et al., "Gene expression analysis by massively parallel signature sequencing (MPSS) on microbead arrays" *Nat. Biotechnol 2000,* Jun. 18(6):630-634, 2000.

Brody, E., and Gold, L., "Aptamers as therapeutic and diagnostic agents" *Molecular Biotechnology,* 2000, 74:5-13.

Bruckbauer, et al., "Writing with DNA and Protein Using a Nanopipet for Controlled Delivery" *JACS,* 2002, A-B.

Bulyk, et al., "Quantifying DNA-protein interactions by double-stranded DNA arrays" *Nature Biotechnology,* Jun. 1999, 17:573-577.

Bustamante C., et al., "Circular DNA Molecules Imaged in Air by Scanning Force Microscopy" *Biochemistry,* 1992, 31:22-26.

Bustamante, C., et al., "Biochemical and structural applications of scanning force microscopy" *Curr. Opin. Struct. Biol.,* 1994 4(5):750-760.

Carr, et al., "High-selectivity pattern transfer process for self-assembled monolayer electron beam resists" *J. Vac. Sci. Technol.,* May/Jun. 1997, 15(3):1446-1450.

Cheng, et al., "Preparation and hybridization analysis of DNA/RNA from *E. coli* on microfabricated bioelectronic chips" *Nature Biotechnology,* 1998, 16:541-546.

Chrisey et al, "Fabrication of patterned DNA surfaces" *Nucleic Acids Research,* (Oct. 1996)24(15):3040-3047.

Clark, M.W. et al., "Nanotechnology tools for functional proteomics analysis" *American Biotechnology Laboratory,* Mar. 2001, 16-18.

Colas, et al., "Genetic selection of peptide aptamers that recognize an inhibit cyclin-dependent kinase 2", *Nature,* Apr. 1996 380(11):548-550.

Colvin, et al. "Semiconductor nanocrystals covalently bound to metal surfaces with self-assembled monolayers" *J. Am. Chem. Soc.,* 1992, 114:5221-5230.

Cui, Y, et al., "Nanowire nanosensors for highly sensitive and selective detection of biological and chemical species" *Science,* 2001, 293, 1289-1292.

Dai, et al., "Nanotube Molecular Wires as Chemical Sensors" *Science,* Jan. 28, 2000, 287:622-625.

Dai, H, et al., "Controlled chemical routes to nanotube architectures" Physics and Devices, *J. Phys. Chem B,* 1999, 103:11246-11255.

Dai, H, et al., "Probing electrical transport in nanomaterials: conductivity of individual carbon nanotubes" *Science,* 1996, 272(5261):523-526.

Dammer, et al., "Binding strength between cell adhesion proteoglycans measured by atomic force microscopy" *Science,* 1995, 267:1173-1175.

Dammer, et al., "Specific antigen/antibody interactions measured by force microscopy" *Biophys. J.,* 1996, 70:2437-2441.

Delamarch, E., et al., "Patterned delivery of immunoglobulins to surfaces using microfluidic networks" *Science,* 1997, 276:779-781.

Ding, Y., Oka, T., et al., "Near-field stimulated TOF nanometric surface mass spectroscopy: characterization of Nano-localized surfaces" Joint International Meeting—200th Meeting of the Electrochemical Society, Inc., 52nd Annual Meeting of the International Society of Electrochemistry, San Francisco, California (2001).

Ding, Y., Ruggero, M. et al., "Development of UHV-STM/TOF hybrid mass analyzer system for nano-characterization of metal silicide surfaces"198th Meeting of the Electrochemical Society, Phoenix, Arizona (2000).

DeRisi, et al., "Exploring the Metabolic and Genetic Control of Gene Expression on a Genomic Scale" *Science,* Oct. 1997, 278:680-686.

Dong, Y. and Shannon, C., "Heterogeneous Immunosensing Using Antigen and Antibody Monolayers on Gold Surfaces with Electrochemical and Scanning Probe Detection" *Anal. Chem.,* 2000, 72:2371-2376.

Dontha, N., et al., "Development of sub-micron patterned carbon electrodes for immunoassays" *J. Pharm. Biomed. Analysis,* (Feb. 1999) 19:83-91.

Dontha, N., et al., "Generation of Biotin/Avidin/Enzyme Nanostructures with Maskless Photoligography" *Anal. Chem.,* 1997, 69: 619-2625.

Dubois, L. et al., "Synthesis, Structure, and Properties of Model Organic Surfaces" *Annu. Rev. Phys. Chem.,* 1992, 43:437-463.

Durbin, S., Feher, G., "Protein crystallization" *Annual Review of Phys Chemistry,* 1996, 47:171-204.

Falvo, M.R., et al., "Bending and buckling of carbon nanotubes under large strain" *Nature*, 1997, 389:582-584.

Fan, S., et al., "Self-oriented regular arrays of carbon nanotubes and their functional devices" *Science*, 1999, 283, 512.

Fang, et al., "Membrane Protein Microarrays" *JACS*, 2002, 124(11):2394-2395.

Farajian, A.A., et al., "Nonlinear Coherent Transport Through Doped Nanotube Junctions" *Physical Review*, Jun. 21, 1999, 82(25):5084-5087.

Feigon, J. "DNA triplexes, quadruplexe, and aptamers" *Clin. Chem.*, 1994, 40(4):647-647.

Fodor, S., et al., "Light-directed spatially addressable parallel chemical synthesis" *Science* 1991, 251: 767-773.

Fodor, S., et al., "Multiplexed biochemical assays with biological chips" *Nature*, 1993, 364:555-557.

Frisbie, C.D., et al., "Functional group imaging by chemical force microscopy" *Science*, 1994, 265:2071-2074.

Fritz, J., et al., "Translating biomolecular recognition into nanomechanics" *Science*, 2000, 316-318.

Fritzsche, W., et al., "Application of Atomic Force Microscopy to Visualization of DNA, Chromatin and Chromosomes" *Critical Reviews™ in Eukaryotic Gene Expression*, 1997, 7(3):231-240.

Fritzsche, W., et al., "Chicken Erythrocyte Nucleosomes Have a Defined Orientation along the Linker DNA-A Scanning Force Microscopy Study" *Scanning*, 1997, 19:42-47.

Fritzsche, W., et al., "Mapping elasticity of rehydration metaphase chromosomes by scanning force microscopy" *Ultramicroscopy*, 1997, 69:191-200.

Fritzsche, W., et al., "Ribosomes substructure investigated by scanning force microscopy and image processing" *Journal of Microscopy*, 1998, 189, Pt 1, 50-56.

Fujihira, et al., "Effect of capillary force on friction force microscopy: a scanning hydrophilicity microscope" *Chemistry Letters*, Jul. 1996, 7:499-500.

Gillen, G., Bennett, J., et al., "Molecular imaging secondary ion mass spectrometry for the characterization of patterned self-assembled monolayers on silver and gold" *Anal. Chemistry*, 1994, 66:2170-2174.

Girault, S., Chassaing, G. et al., "Coupling of MALDI-TOF mass analysis to the separation of biotinylated peptides by magnetic streptavidin beads" *Anal. Chemistry* 1996, 68:2122-2126.

Grabar, et al., "Preparation and characterization of Au colloid monolayers" *Anal. Chem.*, 1995, 67(4):735-743.

Haab, et al., "Protein microarrays for highly parallel detection and quantitation of specific proteins and antibodies in complex solutions" *Genome Biology*, 2001, 2(2)0004.1-0004.13.

Hansma, H.G., et al., "Atomic force microscopy of long and short double-stranded, single-stranded and triple-stranded nucleic acids" *Nuc. Acids Res.*, 1996, 24(4):713-720.

Hansma, H.G., et al., "Recent advances in atomic force microscopy of DNA" *Scanning* 1993, 15(5):296-9.

Hansma, H.G., Sinsheimer, R.L., et al., "Atomic force microscopy of single- and double-stranded DNA" *Nucleic Acids Research* 1992, 20:3585-90.

Hansma, P.K., et al., "Tapping mode atomic force microscopy in liquids" *Appl. Phys. Lett.*, 1994, 64(13):1738-1740.

Heller, et al., "Discovery and analysis of inflammatory disease-related genes using cDNA microarrays" *PNAS USA*, 1997, 94: 2150-2155.

Henderson, E., "Atomic force microscopy of conventional and unconventional nucleic acid structures" *Journal of Microscopy*, 1992, 77-84.

Henderson, E., "Imaging and nanodissection of individual supercoiled plasmids by atomic force microscopy" *Nuc. Acids Res.*, 1992, 20(3):445-447.

Henderson, E., "Imaging of Living Cells by Atomic Force Microscopy" *Progress in Surface Science*, May 1994, 46(1):39-60.

Henderson, E., "Molecular force detection and spectroscopy with the atomic force microscope" *Science Progress*, 1998, 81(2):141-151.

Henderson, E., et al., "Actin Filament Dynamics in Living Glial Cells Imaged by Atomic Force Microscopy" *Science*, 1992, 257:1944-1946.

Henderson, E., et al., "New Ribosome Structure" *Science*, 1984, 255:510-512.

Henderson, E., et al., "Telomeric DNA oligonucleotides form novel intramolecular structures containing guanine-guanine base pairs" *Cell*, 1987, 51(6):899-908.

Henderson, et al., "A method for gold coating experimental detector beampipes" http://www.Ins.cornell.edu/public/CBN/1999/CBN99-7/cbn99-7.pdf, 1999.

Hiller, et al., "Microarrayed allergen molecules: diagnostic gatekeepers for allergy treatment" *FASEB*, 2002, 16:414-416.

Hinterdorfer, P. et al., "Detection and localization of individual antibody-antigen recognition events by atomic force microscopy" *PNAS*, 1996, 93:3477-3481.

Hoh, J.H., and Hansma, P.K., "Atomic force microscopy for high resolution imaging in cell biology" *Trends in Cell Biology*, 1992, 2:208-213.

Hoh, J.H., et al., "Atomic force microscopy and dissection of gap junctions" *Science*, 1991, 1405-1408.

Hoh, J.H., et al., "Quantized adhesion detected with the atomic force microscope" *J. Am. Chem. Soc.*, 1992, 114:4917-4918.

Hong, et al., "A new tool for studying the in situ growth processes for self-assembled monolayers under ambient conditions" *Langmuir*, 1999, 15:7879-7900.

Hong, et al., "Multiple ink nanolithography: toward a multiple-pen nano-plotter" *Science*, 1999, 286:523-525.

Hong, S. et al. "A Nanoplotter with Both Parallel and Serial Writing Capabilities" *Science*, Jun, 9, 2000, 288:1808-1811.

Hovis, et al., "Cyloaddition chemistry and formation of ordered organic monlolayers on silicone (001) surfaces" *Surface Science*, 1998, 402-404, pp. 1-7.

Hovis, et al., "Structure and bonding of ordered organic monolayers of 1,5-cyclooctadiene on the silicon (001) Surface" *J. Phys. Chem. B.*, 1997, 101: 9581-9585.

Hu, et al., "Imaging the condensation and evaporation of molecularly thin films of water with nanometer resolution" *Science*, 1995, 268(5208):267-269.

Huck, et al., "Patterned polymer multilayers as etch resists" *Langmuir*, 1999, 15:6862-6867.

Ivanisevic, et al., "Dip-Pen Nanolithography on Semiconductor Surfaces" *J. Am. Chem. Soc.*, 2001, 123:7887-7889.

Iyer, et al., "The Transcription Program in the Response of Human Fibroblasts to Serum" *Science*, 1999, 283(5398):83-87.

Jackman, et al., "Fabrication of submicrometer features on curved substrates by microcontact printing" *Science*, 1995, 269: 664-666.

James, et al., "Patterned protein layers on solid substrates by thin stamp microcontact printing" *Langmuir*, 1998, 14:741-744.

Janes, et al., "Electronic conduction through 2D arrays of nanometer diameter metal clusters" *Superlattices and Microstrucures*, 1995, 18(4):275-282.

Jaschke, et al., "Deposition of organic material by the tip of a scanning force microscope" *Langmuir*, 1995, 11:1061-1064.

Jin, X., Unertl, W., "Submicrometer modification of polymer surfaces with a surface force microscope" *Applied Physics Letters*, 1992, 61(6): 657-659.

Jones, V., et al., "Microminiaturized Immunoassays Using Atomic Force Microscopy and Compositionally Patterned Antigen Arrays 66" *Anal. Chem.*, 1998, 70(7):1233-1241.

Karpovich, et al., "Direct measurement of the adsorption kinetics of alkanethioilate self-assembled monolayers on microcrystalline gold surface" *Langmuir*, 1994, 10:3315-3322.

Kim, et al., "Nanotube nanotweezers" *Science*, Dec. 10, 1999, 286:2148-2150.

Knezevic et al., "Proteomic profiling of the cancer microenvironment by antibody arrays" *Proteomics*, 2001,. 1:1271-1278.

Kochanek, et al., "Transcriptional silencing of human ALU sequences and inhibition of protein binding in the box B regulatory elements by 5'CG3" methylation" *FEBS Lett.*, 1995, 360(2):115-120 [PMID 7875314] Abstract.

Komeda, et al., "Octadecyltrichlorosilane self-assembled-monolayer islands as a self-patterned-mask for HF etching of $SiO_2$ on Si" *J. Vac. Sci. Technol A.*, 1998, 16(3):1680-1685.

Kumar, et al., "The use of self-assembled monolayers and a selective etch to generate patterned gold features" *J. Am. Chem. Soc.*, 1992, 114:9188-9189.

Lahiri, et al., "Patterning ligands on reactive SAMs by microcontact printing" *Langmuir*, 1999, 15:2055-2060.

Laibinis et al., "ω-terminated alkanethiolate monolayers on surfaces of copper, silver, and gold have similar wettabilities[1]" *J. Am. Chem. Soc.*, 1992, 114: 1990-1995.

Lal, R. and John, S.A., "Biological applications of atomic force microscopy" *Am J. Physiology*, 1994, 266(1):1-21.

Lanio, T., et al., "PCR-based random mutagenesis method using spiked oligonucleotides to randomize selected parts of gene without any wild-type background" *Biotechniques*, 1998, 25(6):958-965.

Lee, et al., "Nanometer-scale lithography on H-passivated Si(100) by atomic force microscope in air" *J. Vac. Sci. Technol. A.*, 1997, 15(3):1451-1454.

Lee, G. et al. "Direct measurement of the forces between complementary strands of DNA" *Science*, 1994, 266:771-773.

Lercel, et al., "Self-assembled monolayer electron-beam resists on GaAs and $SiO_2$," *J. Vac. Sci. Technol. B.*, 1993, 11 (6):2823-2828.

Lercel, et al., "Sub-10nm lithography with self-assembled monolayers" *Appl. Phys. Lett.*, 1996, 68(11):1504-1506.

Liu, et al., "Nanofabrication of self-assembled monolayers using scanning probe lithography" *Acc. Chem. Res.*, 2000, 33(7):457-466.

Lo, et al., "Organic and inorganic contamination on commercial AFM cantilevers" *Langmuir*, 1999, 15:6522-6526.

Lüthi, et al., Parallel nanodevice fabrication using a combination of shadow mask and scanning probe methods: *Applied Physics Letters*, 1999, 75(9):1314-1316.

Lutwyche, et al., "5×5 2D AFM cantilever arrays a first step towards Terabit storage device" *Sensors and Actuators*, 1999, 73:89-94.

Lynch, M., et al., "A Reliable Preparation Method for Imaging DNA by AFM" *Microscopy Today*, 1999, 99(9) 1 pg.

Lyubchenko, Y.L., et al., "Atomic force microscopy of DNA and bacteriophage in air, water and propanol: The role of adhesion forces"*Nuc. Acids Res.*, 1993, 21(5):1117-1123.

Macaya, et al., "Thrombin-binding DNA aptamer forms a unimolecular quadruplex structure in solution" *PNAS USA*, Apr. 1993, 90:3745-3749.

MacBeath, G. and Schreiber, S.L., "Printing Proteins as Microarrays for High-Throughput Function Determination" *Science*, Sep. 8, 2000, 289:1760-1763.

Magno, R., Bennett, B., "Nanostructure patterns written in III-V semiconductors by an atomic force microscope" *Applied Physics Letters*, 1997, 70(14):1855-1857.

Malmborg, et al., "Real Time Analysis of Antibody-Antigen Reaction Kinetics", *Scand. J. Immunol.*, 1992, 35:634-650.

Marsh, T.C., et al., "A new DNA nanosctructure imaged by scanning probe microscopy" *Nuc. Acids Res.* 1995, 23(4):696-700.

Marsh, T.C., et al., "G-wires: Self-assembly of a telometic oligonucleotide, d(GGGGTTGGGG), into large superstructures" *Biochemistry* 1994, 33:10718-10724.

Martin, B., et al., "Ortogonal Self-Assembly on Colloidal Gold-Platinum Nanorods" *Advanced Materials*, 1999, 11:1021.

Matteucci, et al., "Synthesis of deoxyoligonucleotides on a polymer support 1" *J. Am. Chem. Soc.*, 1981, 103:3185-3191.

Maynor, et al., "Au :Ink" for AFM "Dip-Pen" Nanolithography *Langmuir*, 2001, 17:2575-2579.

Mazzola, L., "Discrimination of DNA hybridization using chemical force microscopy" *Biophysical Journal*, 1999, 76:2922-2933.

McEuen, et al., "Crossed Nanotube Junctions" *Science*, Apr. 21, 2000, 288:494-497.

Meister, et al., "Nanoscale Dispensing of Liquids through Cantilevered Probes" *MNE '02*, Lugano Switzerland, Sep. 16-19, 2002.

Mendoza, et al., "High-Throughput Microarray-Based Enzyme-Linked Immunosorbent Assay (ELISA)" *BioTechniques*, 1994, 27(4):778-788.

Meyer, G. and N.M. Amer, "Novel optical approach to atomic force microscopy" *Appl. Phys. Lett.*, 1988, 53:1045-1047.

Minne, et al., "Centimeter scale atomic force microscope imaging and lithography" *Applied Physics Letters*, 1998, 73(12):1742-1744.

Minne, S.C., et al., "Automated parallel high-speed atomic force microscopy" *Appl. Phys. Lett.*, 1998, 72(18):2340-2342.

Mirkin, et al., "Dip-Pen Nanolithography: Controlling Surface Architecture on the Sub-100 Nanometer Length Scale" *Chemphyschem*, 2001, 2:37-39.

Mirkin, et al., "Programming the Assembly of Two- and Three-Dimensional Architectures with DNA and Nanoscale Inorganic Building Blocks" Invited Contribution from Recipient of ACS Award in Pure Chemistry *Inorg. Chem.*, 2000, 39:2258-2272.

Mosher, C., et al., "NanoArrays, The Next Generation Molecular Array Format for High Throughput Proteomics, Diagnostics and Drug Recovery" *JALA*, 2000, 5(5):75-83.

Moy, et al., "Intermolecular Forces and Energies Between Ligands and Receptors" *Science,* 1994, 266:257-259.

Moy, V.T., et al., "Probing the forces between complimentary strands of DNA with the atomic force microscope" *SPIE,* 1995, 2384:2-12.

Mueller, et al., "Atomic force microscopy deposition of poly-l-lysine structures onto lipid bilayers supported by mica" *Langmuir,* 2000, 16:9568-9570.

Müller, et al., "Nanostructuring of alkanethiols with ultrastrap field emitters" *J. Vac. Sci Technol. B.,* 1995, 13(6):2846-2849.

Murray, et al., "Atomic force microscopy of biochemically tagged DNA" *Proc., Natl., Acad. Sci.,* 1993, 90:3811-3814.

Musil, C., Nanostructuring of gold electrodes of immunosensing applications: *J. Vac. Sci. Technol. B.,* 1995, 13(6):2781-2786.

Niu, et al., "Atomic force microscopy of DNA-colloidal gold and DNA-protein complexes" *SPIE Advances in DNA Sequencing Technology,* 1993, 1891:71-77.

Noy, et al., "Chemical force microscopy: exploiting chemically-modified tips to quantify adhesion, friction, and functional group distributions in molecular assemblies" *J. Am. Chem.,* 1995, 117:7943-7951.

Noy, et al., "Chemically-sensitive imaging in tapping mode by chemical force microscopy: relationship between phase lag adhesion" *Langmuir,* 1998, 14:1508-1511.

Nuzzo, R., "Spontaneously organized molecular assemblies. 3. Preparation and properties of solution adsorbed monolayers of organic disulfides on gold surfaces" *J. Am. Chem. Soc.,* 1987, 109:2358-2368.

Nyffenegger, et al., "Nonometer scale surface modification using the scanning probe microscope: progress since 1991" *Chem. Rev.,* 1997, 97:1195-1230.

O'Brien, J., et al., "Immunosensing Platforms Using Spontaneously Absorbed Antibody Fragments on Gold" *Analytical Chemistry,* 2000, 72(4)703-710 [PMID 10701253] Abstract.

Oshio, T. et al., "Atomic force microscopy detection system using an optical fiber heterodyne interferometer free from external disturbances" *Ultramicroscopy* 42-44 (Jul. 1992) 310-314.

Paweletz, et al., "Reverse phase protein microarrays which capture disease progression shoe activation of pro-survival pathways at the cancer invasion front" *Oncogen,* 2001, 20:1981-1989.

Pawlak, et al., "Zeptosens' protein microarrays: A novel high performance microarray platform for low abundance protein analysis" *Proteomics,* 2002,. 2:383-393.

Perkins, et al., "Fabrication of 15 nm wide trenches in Si by vacuum scanning tunneling microscope lithography of an organosilane self-assembled film and reactive ion etching" *Appl. Phys. Lett.,* 1996, 68(4):550-552.

Pfannschmidt, et al., "Sequence-specific labeling of superhelical DNA by triple helix formation and psoralen crosslinking" *Nucleic Acids Research,* 1996 24(9):1702-1709.

Piner, et al., "Improved imaging of soft materials with modified AFM tips" *Langmuir,* 1999, 15:5457-5460.

Piner, R.D., et al., "Dip-Pen Nanolithography" *Science,* Jan. 29, 1999,283(5402):661-663.

Piner, Richard, "Effect of water on lateral force microscopy in air " *Langmuir,* 1997, 13:6864-6868.

Putnam, C.A.J., "Tapping atomic force microscopy in liquids" *Appl. Phys. Lett.,* 1994, 64(18):2454-2456.

Qin, et al., Fabrication of ordered two-dimensional arrays of micro- and nanoparticles using patterned self-assembled monolayers as templates: *Adv. Matter,* 1999, 11(17):1433-1437.

Rankin, P.C. Wilson, A.T. "The Surface Chemistry of the Mica-Aluminum-Sulfate System" *Journal of Colloid and Interface Science,* (1969) 30(3):277-282.

Reed, et al., "Conductance of molecular junction" *Science,* 1997, 278:252-254.

Rief, et al., "Reversible unfolding of individual Titin Ig-domains by AFM" *Science,* 1997, 276:1109-1111.

Rief, M., et al., "Single Molecule Force Spectroscopy on Polysaccharides by Atomic Force Microscopy" *Science,* 1997, 275:1295-1297.

Rief, M., et al., "The mechanical stability of immunoglobulin and fibronectin III domains in the muscle protein titin measured by atomic force microscopy" *Biophysical Journal,* 1998, 3008-3014.

Robinson, et al., Autoantigen microarrays for multiplex characterization of autoantibody responses *Nature Medicine,* Mar. 2002, 8(3):1-7.

Santos, et al., "Probing hydrophobic interactions of surfaces and macromolecules with atomic force microscope" *Book of Abstracts,* 214 ACS National meeting, Sep. 7-11, 1997, PHYS-248.

Sastry, et al., "Formation of patterned hetrocolloidal nanoparticle thin films" *Langmuir,* 2000, 16:3553-3556.

Schaus, S., et al., "Cell Viability and Probe-Cell Membrane Interactions of XR1 Glial Cells Imaged by Atomic Force Microscopy" *Biophysical Journal,* Sep. 1997, 73:1205-1214.

Schena, et al., "Parallel human genome analysis : Microarray-based expression monitoring of 1000 genes" *PNAS USA,* 1996, 93:10614-10619.

Schena, M., *Microarray Biochip Technology,* Eaton Publishing, NatickMA 2000. (Book Reference Not Being Provided).

Schoer, et al., "Scanning probe lithography. 4. Characterization of scanning tunneling microscope-induced patterns in *n*-Alknethiol self-assembled monolayers" *Langmuir,* 1997, 13:2323-2332.

Schumacher, et al., "Nanomachining of mesoscopic electronic devices using an atomic force microscope" *Applied Physics,* 1999, 75(8):1107-1109.

Schwartz, et al. "Meniscus Force Nanografting: Nanoscopic Patterning of DNA" *Langmuir,* 2001, 17:5971-5977.

Schwartz, et al., "Molecular Transport from an Atomic Force Microscope Tip: A Comparative Study of Dip-Pen Nanolithography" *Langmuir,* American Chemical Society, Nov. 6, 2001.

Schweitzer, et al., "Multiplexed protein profiling on microarrays by rolling-circle amplification" *Nature Biotechnology,* Apr. 2002, 20:359-365.

Shaiu, W.L., et al., "Atomic Force Microscopy of Oriented Linear DNA Molecules Labeled with 5nm Gold Spheres" *Nuc. Acids Res.,* 1993, 21(1):99-103.

Shaiu, W.L., et al., "Visualization of circular DNA molecules labeled with colloidal gold spheres using atomic force microscopy" *J. Vac. Sci. Technol. A.,* 11(4):820-823.

Sheehan, et al., "Thiol diffusion and the role of humidity in "dip pen" nanolithography" *Physical Review Letters,* Apr. 15, 2002, 88(15):156104-1-156104-4.

Sheen, et al., "A new class of organized self-assembled monolayers: alkane thiols on GaAs (100)" *J. Am. Chem. Soc.,* 1992, 114:1514-1515.

Sherman, Chemical Vapor Deposition For Microelectornices: Principles, Technology and Applications (Noyes, Park Ridges, NJ, 1987). (Book Reference Not Being Provided).

Shlyakhtenko, L.S., et al., "Structure and dynamics of supercoil-stabilized DNA cruciforms" *J. Mol. Biol.,* 1998, 280(1):61-72.

Shlyakhtenko, L.S., Gall, A.A., et al., "Atomic force microscopy imaging of DNA covalently immobilized on a functionalized mica substrate" *Biophysical Journal,* Jul. 1999, 77:568-576.

Silzel, et al., "Mass-sensing, multianalyte microarray immunoassay with imaging detection" *Clinical Chemistry,* 1998, 44(9):2036-2043.

Smalley, et al., "Nanotube Device" *Science,* Oct. 3, 1997, 278:100-103.

Smith et al., "Overstretching B-DNA: the elastic response of individual double-stranded and single stranded DNA molecules" *Science,* Feb. 9, 1996, 271:795-799.

Snow, et al., "High speed patterning of a metal silicide using scanned probe lithography" *Applied Physics Letters,* 1999, 75(10):1476-1478.

Soh, H., et al., "Integrated nanotube circuits: controlled growth and ohmic contacts to single-walled-carbon nanotubes" *Appl. Phys. Letts.,* 1999, 75(5):627-629.

Sondag-Huethorst, et al., "Generation of electrochemically deposited metal patterns by means of electron beam (nano)lithography of self-assembled monolayer resists" *Appl. Phys. Lett.* 1994, 64(3):285-287.

Southern, E.M., "Detection of specific sequences among DNA fragments separated by gel electrophoresis" *J. Mol. Biol.* 1975, 98:503-517.

Spectroscopy Europe—News Feb./Mar. 2002, 6 pages, http://www.spectroscopyeurope.com/news14_1.html.

Spence, J., Weierstall, U., et al., "Atomic species identification in scanning tunneling microscopy by time of flight spectroscopy" *J. Vac. Sci. Tech.,* 1996, B14(3):1587-1590.

Sreekumar, et al., "Profiling of cancer cells using protein microarrays: Discovery of novel radiation-regulated proteins" *Cancer Research,* 2001, 61:7585-7593.

Steiner, et al., "Adsorption of alkanenitriles and alkanedinitriles on gold and copper" *Langmuir,* 1992, 8:2271-2777.

Stöckle, R., Setz, P. "Nanoscale Atmospheric Pressure Laser Ablation-Mass Spectrometry" *Anal. Chem.,* 2001, 73(7):1399-1402.

Su, et al., "Moving beyond Molecules: Patterning Solid-State Features via Dip-Pen Nanolithography with Sol-Based Inks" *JACS,* 2002, 124(8):1560-1561.

Sun, et al., "Nanoscale Molecular Patterns Fabricated by Using Scanning Near-Field Optical Lithography" *JACS,* 2002, 124(11):2414-2415.

Tang, K., Fu, D., et al., "Matrix-assisted laser desorption/ionization mass spectrometry of immobilized duplex DNA probes" *Nucleic Acids Research,* 1995, 23(16):3126-3131.

Tans, et al., "Room-temperature transistor based on a single carbon nanotube" *Nature,* May 7, 1998, 393:49-52.

Tarlov, M.J., Newman, J.G., et al., "Static secondary ion mass spectrometry of self-assembled alkanethiol monolayers on gold" *Langmuir,* 1992, 8:1398-1405.

Tien, et al., "Microfabrication through electrostatic self-assembly" *Langmuir,* 1997, 13:5349-5355.

Troughton, E., Bain, C., et al., "Monolayer films prepared by the spontaneous self-assembly of symmetrical and unsymmetrical dialkyl sulfides from solution onto gold substrates: Structure, properties and reactivity of constituent functional groups" *Langmuir,* 1988, 4:365-385.

Tsukamoto, et al. "Twin-probe scanning tunneling microscope" *Rev. Sci. Instrum.,* Jul. 1991, 62(7):767-1771.

Uetz, P., et al., "A comprehensive analysis of protein-protein interactions in *Saccharomyces cerevisiae" Nature,* Feb. 10, 2000, 403(6770):623-627.

Ulman, Abraham, "Formation and structure of self-assembled monolayers" *Chem. Rev.,* 1996, 96:1533-1554.

Ulman, An Introduction To Ultrathin Organic Films: From Langmuir-Blodgett to Self-Assembly (Academic, Boston 1991) (Alkanethiols on gold). (Book Reference Not Being Provided).

Vesenka, J. et al., "A substrate preparation for reliable imaging of DNA molecules with the scanning force microscope" *Ultramicroscopy,* 1992, 42-44:1243-1249.

Vesenka, J., et al., "Colloidal gold particles as an incompressable atomic force microscope imaging standard for assessing the compressability of biomolecules" *Biophys. J.,* 1993, 65:992-997.

Vesenka, J., et al., "Combining optical and atomic force microscopy for life sciences research" *BioTechniques,* 1995, 19(2):240-253.

Vettiger, et al., "Ultrahigh density, high-data-rate NEMS-based AFM data storage system" *Microelectronic Engineering,* 1999, 46:11-17.

Vezenov, Dmitri, "Force titrations and ionization state sensitive imaging of functional groups in aqueous solutions by chemical force microscopy" *J. Am. Chem. Soc.,* 1997, 119:2006-2015.

Vossmeyer, et al., "Combinatorial approaches toward patterning nanocrystals" *Journal of Applied Pysics,* 1998, 84(7):3664.

Wadu-Mesthrige, et al., "Fabrication and imaging of nanomneter-sized protein patterns" *Langmuir,* 1999, 15:8580-8583.

Wallraff, et al., "Lithographic imaging techniques for the formation of nanoscopic features" *Chem. Rev.,* 1999, 99:1801-1821.

Walters, D.A., Hampton, A.D., et al. "Atomic force microscope integrated with a scanning electron microscope for tip fabrication" *Applied Physics Letters,* Aug. 8, 1994, 65(6):787-789.

Wang, et al., "Nanometer scale patterning and pattern transfer on amorphous Si, crystalline Si, and $SiO_2$ surfaces using self-assembled monolayers" *Appl. Phys. Lett.,* 1997, 70(12):1593-1595.

Weierstall, U. Spense, J. "Atom species identification in STM using an Imaging Atom-Probe technique" *Surface Science* 1998, 398: 267-279.

Whitesides, et al., "Self-assembled monolayers and lithography" *Nanophase Chemistry* 1995, 39: 109-122.

Wilbur, et al., "Scanning force microscopes can image patterned self-assembled monolayers" *Langmuir,* 1995, 11:825-831.

Williamson, et al., "G-quartets in biology: Reprise" *PNAS USA,* Apr. 15, 1993, 90(8):3124-3124.

Williamson, et al., "Monovalent cation-induced structure of telomeric DNA: The G-quartet model" *Cell,* 1989, 59(5):871-880.

Wilson, et al., "Surface organization and nanopatterning of collagen by dip-pen nanolithography" *PNAS,* Nov. 20, 2001, 98(24):13660-13664.

Wong, S., et al., "Covalently functionalized nanotubes as nanometre-sized probes in chemistry and biolog" *Nature,* 1998, 394:52-55.

Wong, S., et al., "Covalently functionalized single-walled carbon nanotube probe tips for chemical force microscopy" *Journal of the American Chemical Society,* 1998, 120:8557-8558.

Wong, S., et al., "Functionalization of carbon nanotube AFM probes using tip-activated gases" *Chem Physics Letters,* 1999, 306:219-225.

Xia, et al., "A selective etching solution for use with patterned self-assembled monolayers of alkanethiolates on gold" *Chem. Mater.,* 1995, 7:2332-2337.

Xia, et al., "Complex optical surfaces formed by replica molding against elastomeric masters" *Science,* 1996, 273: 347-349.

Xia, et al., "Pattern transfer: self-assembled monolayers as ultrathin resists" *Microelectronic Engineering,* 1996, 32:255-268.

Xia, et al., "Soft lithography" *Agnew Chem. Int. Ed.,* 1998, 37:551-575.

Xia, et al., "Unconventional methods for fabricating and patterning nanostructures" *Chem. Rev.,* 1999, 99:1823-1848.

Xu, et al., "Fabrication of nanometer scale patterns within self-assembled monolayers by nanografting" *Langmuir,* 1999, 15:7244-7251.

Xu, et al., Nanometer-scale fabrication by simultaneous nanoshaving and molecular self-assembly: *Langmuir,* 1997, 13:127-129.

Xu, et al., "Wetting and capillary phenomena of water on mica" *J. Phys. Chem. B.,* 1998, 102:540-548.

Yan Li, et al., "Electrochemical AFM "Dip-Pen" Nanolithography" *J. Am. Chem. Soc.* 2001, 123:2105-2106.

Yan, et al. "Patterning as performed, reactive SAM using microcontact printing" *J. Am. Chem. Soc.,* 1998, 120:6179-6180.

Yan, et al., "Patterning thin films of poly(ethylene imine) on a reactive SAM using microcontact printing" *Langmuir,* 1999, 15:1208-1214.

Ying, et al., "Programmable Delivery of DNA through a Nanopipet" *Anal. Chem.,* 2002, 74:1380-1385.

Youil, R., Screening for mutations by enzyme mismatch cleavage with T4 endonuclease VII *PNAS USA,* 1995, 92(1):87-91.

Zhong, Q., et al., "Fractured polymer/silica fiber surface studied by tapping mode atomic force microscopy" *Surf. Sci. Lett.,* Jan. 3, 1993, 290: L 688-L692.

Zhu, et al., "Analysis of yeast protein kinases using protein chips" *Nature Genetics,* 2000, 26:283-289.

Zhu, et al., "Global Analysis of Protein Activities Using Proteome Chips" *Science,* Sep. 2001, 293(14):2101-2105.

* cited by examiner

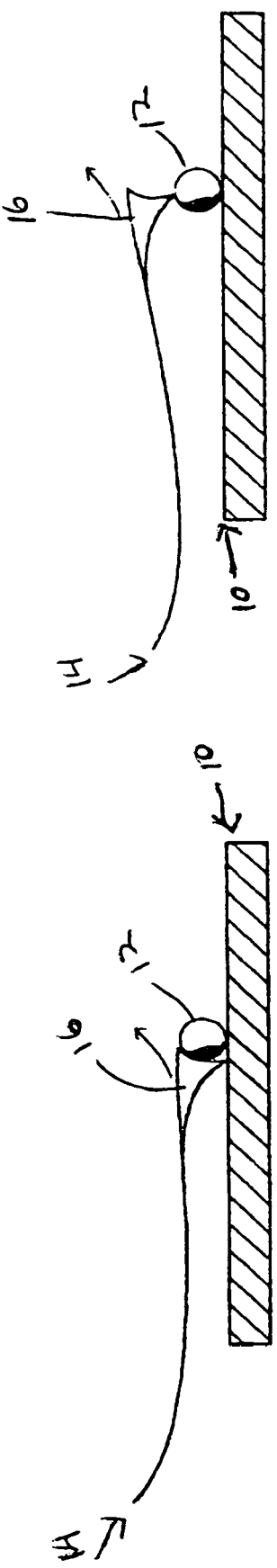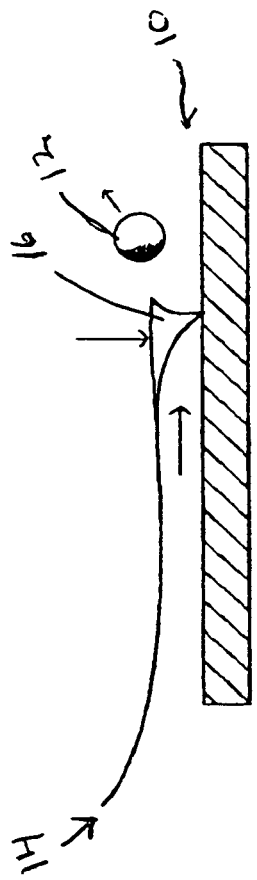
Fig. 1a
Fig. 1b
Fig. 1c

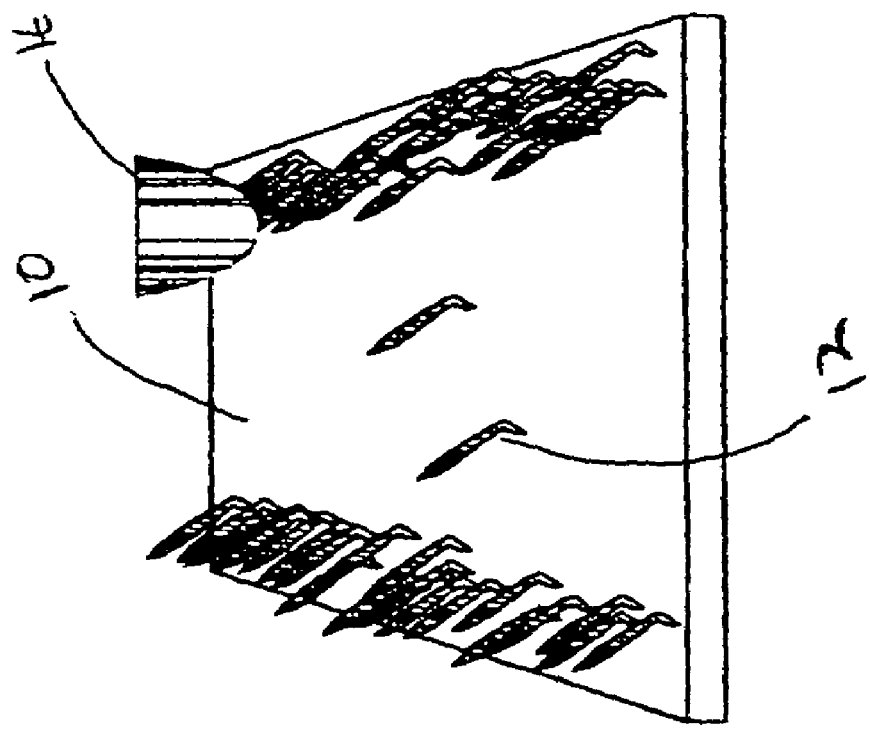
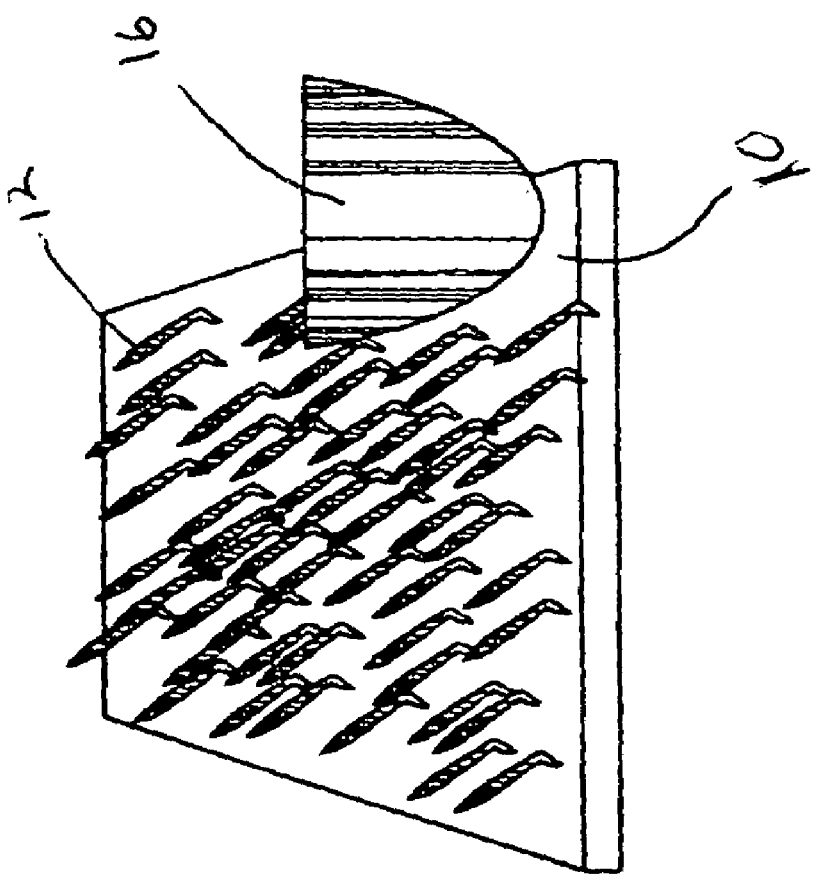
Fig. 3a
Fig. 3b

EVALUATING BINDING AFFINITIES BY FORCE STRATIFICATION AND FORCE PANNING

PRIORITY

This application is a continuation of U.S. patent application Ser. No. 09/974,757, filed Oct. 9, 2001, now abandoned, which claims priority to U.S. Provisional Patent Application Ser. No. 60/238,566, filed Oct. 10, 2000, each of which is incorporated herein by reference.

TECHNICAL FIELD

The present invention is a method for the analysis of objects bound to a surface, or materials on a surface, as a function of the interactive molecular forces between them. More specifically, the present invention is a method for the differentiation and evaluation of objects by their binding affinity.

BACKGROUND

Measuring the binding affinity between materials, molecules, and cells is key to a broad spectrum of industries, including but not limited to, material development, semiconductor production, bioanalytical assays, biomedical diagnostics, and drug discovery. With the emergence of solid state array-based bioanalytical and genetic diagnostic instruments and related equipment, new methods for cost effective screening of a large number of reactions in a miniaturized solid state form have become increasingly desirable.

The favored approach to date is to monitor changes in optical properties, usually fluorescence, when a known, fluorescently labeled molecule interacts with a known molecular species at a specific address in a molecular array. These apparatuses and methods, however, often impose stereochemical constraints by the addition of reporter systems to the molecules used to interrogate the molecular array. Furthermore, these methods do not directly report the actual binding affinity. Thus, label free, direct interrogation of molecular binding affinities using a micromechanical reporter is of obvious utility. More sophisticated and robust methods of this interrogation are required to better analyze a range of different objects bound, adsorped, or otherwise attached to a variety of surfaces.

One method for the direct detection of whether a molecule or other object is bound to a surface, or an object on the surface, is the scanning probe microscope. One type of scanning probe microscope is the atomic force microscope ("AFM"). In the AFM, a sharp probe is situated at the end of a flexible cantilever and scanned over a sample surface. While scanning, the probe and cantilever are deflected by the net sum of the attractive and repulsive forces between a tip of the probe and the surface and/or objects deposited on the surface. The deflection of the cantilever is usually measured by the reflection of a focused laser beam from the back of the cantilever onto a split photodiode, constituting an "optical lever" or "beam deflection" mechanism. The change in deflection indicates the presence of an object on the surface. These previous methods utilized materials bound to the probe to indicate the resultant force interactions between the probe and the material bound on the surface. Other methods for the detection of cantilever deflection include interferometry and piezoelectric strain gauges.

The first AFMs recorded only the vertical displacements of the cantilever. More recent methods also involve recording the torsional force, resonating the tip and allowing only transient contact, or in some cases no contact at all, between the probe and the sample. Plots of the tip displacement of the probe, or resonance changes as it traverses a sample surface, are used to generate topographic images. Such images have revealed the three dimensional structure of a wide variety of sample types including material, chemical, and biological specimens. Some examples of the latter include DNA, proteins, chromatin, chromosomes, ion channels, and even living cells. These prior methods, however, are limited to those complexes that can be bound to the probe and then dragged across the various materials on a surface. A new method is needed that is not limited in this manner.

In addition to its imaging capabilities, the AFM can make extremely fine force measurements. The AFM can directly sense and measure forces in the microNewton ($10^{-6}$) to picoNewton ($10^{-12}$) range. Thus, the AFM can apply forces to, and measure forces between, molecular pairs, and even single molecules. Moreover, the AFM can measure and apply a wide variety of other forces and phenomena, such as magnetic fields, thermal gradients and viscoelasticity. This ability can be exploited to map force fields on a sample surface, and reveal with high resolution the location and magnitude of these fields, as in, for example, localizing complexes of interest located on a specific surface. Furthermore, to make additional molecular force measurements, the AFM probe may be functionalized with a molecule of interest.

Previous methods of evaluating the mechanical force necessary to remove bound objects to a surface included combinatorial chemistry techniques like repetitively binding one or more objects to a surface followed by washing the objects away. In this manner a characterization of how well the objects bound or adsorped to the surface could be determined based on population averages. A need exists for a cost effective and practical improvement to this methodology that results in a characterization of the force required to move objects residing on a surface.

A need exists for a simple and efficient method of quickly assessing the affinity of a bound molecule, cell, or other object to a surface. This method should overcome the prior art limitations of having to drag the material across a surface while attached to a probe, or having to sequentially wash microtiter plates to determine the affinity based on overall population samples. This method should also allow for the determination of binding affinities between the object and other materials that are bound to the surface. Finally, a need exists for a method for eliminating the poorly bound objects on the surface of interest so that the more tightly bound objects can be harvested for further study.

BRIEF DESCRIPTION OF DRAWINGS

FIG. 1a is an elevational side view of a probe contacting an object on a surface and exerting vertical force on the object.

FIG. 1b is a elevational view of the probe of FIG. 1a riding over the top of the object on the surface.

FIG. 1c is an elevational view of a vertical probe force dislodging the object of FIG. 1a.

FIG. 3a is a front perspective view of a surface that includes a number of phage particles adhered to the surface before the probe scans the surface.

FIG. 3b is a front perspective view of the surface of FIG. 3a after the weakly bound phage particles have been removed by scanning the surface with the probe.

SUMMARY

Figure 2B:
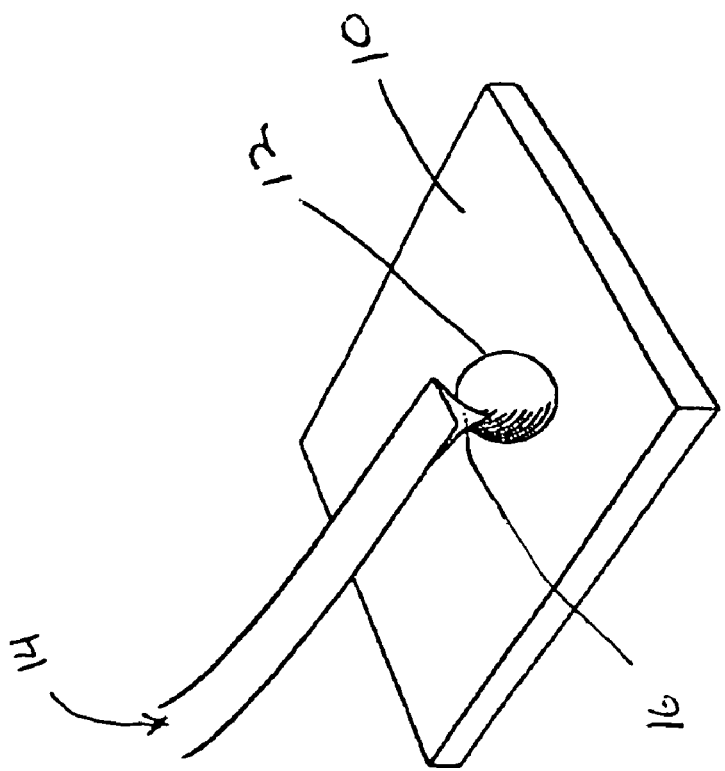
FIG. 2b is an elevational view of the probe exerting torsional force and riding past the object on the surface.

The present invention is a method by which a force transduction device is used to differentially separate and/or remove objects that are bound to on a surface by regulating an applied force. By incrementally increasing the applied force, one can determine the strength of binding between the surface and the objects on the surface. The objects may include, but are not limited to, molecules, viruses, cells, phage, and other organic or inorganic molecules. The process can be carried out on patterned surfaces for rapid and inexpensive screening of large numbers of binding interactions in order to categorize those with a higher binding affinity to the surface. The present invention can also be utilized to characterize the binding affinity between an object and some material placed on the surface.

As an AFM, and the probe attached thereto, is scanned over a surface, a tip of the probe pushes against objects it encounters generating torsion and deflection of the probe. The force exerted on a given object by the tip is related to both the torsional and vertical spring constants of the probe. Measurement of either the torsional and/or vertical probe displacement can be used to qualitatively and quantitatively assess the binding affinity between the object and the surface. For vertical forces, the spring constant is used to calculate the force applied. For torsion based measurements, the degree of twisting of the probe may be measured and multiplied by a known torsional spring constant for the probe to generate a value corresponding to the force necessary for the degree of twisting motion observed. Furthermore, each group of objects that are removed from the surface can be collected for further studying.

The present invention may be particularly useful in developing and studying materials with specific binding properties, drugs and drug inhibitors, diagnostic assays delineating biomolecular binding strengths, protein-protein interaction screens, virus-antibody binding screens receptor-ligand, virus-virucell-substrate, virus-substrate, as well as many others.

The present invention also includes a method for determining the binding affinity between an object and a surface comprising affixing at least one object to a surface, scanning the surface with a scanning probe microscope for locating at least one object affixed to the surface, applying a force to at least one object on the surface to remove at least one object that has a relatively low binding affinity to the surface, monitoring the force applied to at least one object, and calculating the binding affinity between at least one object and the-surface from the force applied to remove at least one object.

Another embodiment of the present invention includes a method for determining a binding affinity between an object and one or more materials, comprising obtaining a surface, the surface further comprising one or more materials deposited thereon, affixing at least one object to be studied to the one or more materials deposited on the surface, scanning the surface with a scanning probe microscope to locate at least one object, and applying a force to at least one object to remove at least one object.

Yet another embodiment of the present invention includes a method for assessing the interaction force between an object and a surface comprising depositing at least one material on a surface, affixing at least one object to the material deposited on the surface, scanning the surface with an atomic force microscope to locate at least one object affixed to the surface, applying a force to at least one object with the atomic force microscope, the force being determined by the user and some of the objects being removed from the surface by this force, scanning the surface to locate the at least one object that is still affixed to the surface, applying a second greater force to the at least one object on the surface using the atomic force microscope, and collecting at least one object still affixed to the surface.

Another embodiment of the present invention includes a method of determining the binding affinity between an object and a surface comprising (a) depositing one or more objects on a surface; (b) scanning the surface with an atomic force microscope to locate the objects on the surface; (c) applying a first force to at least one object on the surface with the atomic force microscope to remove at least one object from the surface that has a relatively low binding affinity;(d) collecting at least one object that has been removed from the surface by the first force;(e) applying a second, greater force to at least one object using the atomic force microscope to remove at least one object from the surface that has a-relatively low binding affinity;(f) collecting at least one object that has been removed from the surface by the second force; and (g) repeating steps (b) through (f).

Yet another embodiment includes a method of determining the binding affinity between an object and a material deposited on a surface comprising (a)depositing at-least one material on a surface; (b) binding at least one object to at least one material; (c) applying a first force to at least one object on the surface with an atomic force microscope; (d) collecting at least one object that has been removed from the surface by the first force; (e) applying a second force to at least one object on the surface using the atomic force microscope to remove at least one object from the surface; (f) collecting at least one object that has been removed from the surface by the second force; (g) repeating steps (b) through (f).

Description of the Embodiments

In the present invention description, the term "object" is utilized to include any material that can be bound to a surface and detected and/or removed using a probe, such as an AFM probe. The objects may be inorganic molecules, organic molecules, biomolecules, proteins, phage particles, cells etc., which are of interest to study. The objects are bound or adsorped to the surface, and thereafter scanned and removed depending on the binding affinity of the object to the surface. Objects may also be bound to another material deposited on the surface. Furthermore, the term "bound" is not limited to covalent bonding, but may include other types of molecular bonding, including adsorption, ionic bonding, as well as specific and non-specific molecular interactions.

The term "relatively" will be utilized to describe the amount of force exerted by the probe upon the object to be studied. The term relatively will only describe the forces in terms of whether the force is high enough to remove the object or so low that the object is not removed. A "relatively low" force is herein used to describe a force that is less than that amount required to displace the object from the surface. A relatively low binding affinity is therefore any binding affinity that results in the object being removed from the surface when the force is applied thereto. A relatively high binding affinity is a binding affinity that is strong enough to withstand the force that is being applied. The "set point" is the amount of force the user wishes to have the probe exert on the object.

The present invention utilizes a standard AFM probe to apply the force to the objects on the surface. The standard AFM probe includes a probe and a tip. The probe connects to the AFM. The deflection of the probe is used to determine the force applied and is further explained herein. The tip contacts the surface and the object bound thereto as it scans across the surface. As may be appreciated, a custom probe or other piece of hardware may be attached and moved by the AFM, or other instrumentation, across the surface. It is merely required that the instrument, probe, and tip be precise enough to apply the desired force to the objects bound either to the surface or the material deposited on the surface.

Finally, the present description utilizes the term "binding affinity" to generally refer to the attraction between the object and the surface, or the material on the surface, to which it is bound. The materials bound to the surface may be bound randomly or may be placed in specific deposition domains to form an array on the surface. Deposition materials, and arrays of the same, are further described in co-pending U.S. application Ser. No. 09/574,519, which is herein incorporated by reference for all it teaches.

With reference for FIGS. 1a–c and 2a–b, a synopsis of the present method invention will be herein described. Afterwards, a more detailed description of the various components of the apparatus will be undertaken followed by a recitation of some specific examples.

The Method

FIG. 1a illustrates a surface 10 on which one or more objects 12 are bound. Objects 12 are bound on the surface 10 utilizing any manner of binding interaction known to those skilled in the art. Various ways in which materials may be bound to the surface include covalent, noncovalent, spontaneous, electrostatic, or other methods known in the art. The objects 12 may be an inorganic or organic molecule, such as a protein or a cell, or a particle, such as a phage particle. The surface 10 and objects 12 will be further described herein.

As illustrated in FIG. 1a, the present invention further comprises a probe 14. The probe 14 utilized herein is a standard silicon nitride atomic force microscopy probe such as is available from Digital Instruments, Santa Barbara, Calif. (not shown). The probe is attached to an AFM instrument that is also available from Digital Instruments. As illustrated in FIG. 1a, the probe 14 may further comprise a tip 16. The tip 16 is that portion of the probe that actually makes contact with the surface 10 and is explained more herein.

The surface 10 (with the objects 12) is then placed into an AFM flow cell and into the liquid medium in which the AFM scans are run. The liquid medium may be selected by one skilled in the art depending on the surface 10 and the objects 12 under study.

In the present embodiment, the AFM is utilized to scan the surface and to detect the location of the objects 12. As illustrated in FIG. 1b, the tip 16 will contact the objects on the surface 10 and, depending on the type of AFM scanning being utilized, will ride over the top of the object 12. During the time that the probe 14 is in contact with the object 12, the probe 14 is deflected due to the interaction of the probe 14 with the object 12. The deflection of the probe 14 is tracked by the AFM instrumentation and so the location and size of the object 12 can be determined and recorded. The utilization of an AFM to run such a scan is well known to those skilled in the art and enables the user of the present invention method to determine the initial location of the objects 12 bound to the surface 10. The present invention utilizes such a step to determine when the objects are removed from the surface during the present invention method. In alternative embodiments, the step of locating the objects 12 may be omitted without changing the nature and scope of the present invention. In still further embodiments the location of the objects 12 may already be known because they were placed on the surface 10 in specific arrays.

Once the location of the objects 12 has been determined, the set point of the AFM is then increased. The increase in the set point may be experimentally determined. Likewise, the set point may be increased in very minute amounts to allow greater stratification of the different binding affinities of the objects 12. Increasing the set point increases the amount of force applied to the objects 12 on the surface 10.

During the second scan, the set point force is exerted upon the objects 12 that are on the surface 10. When the tip 16 of the probe 14 contacts the objects 12, if the force is less than that required to move or displace the object 12, the tip 16 and the probe 14 will ride up over the object 12 as is illustrated in FIG. 1b. In this case, the relatively high binding affinity of the object 12 with the surface 10 is not broken by the relatively low force exerted on the object 12. If the force exerted by the tip 16 and the probe 14 is relatively higher than the binding affinity between the object 12 and the surface 10, however, the force may remove the object 12 from the surface. See FIG. 1c.

As may be further appreciated by those skilled in the art, the probe 14 may be deflected by the force it is exerting on the object 12 up to the point where the force exerted overcomes the binding affinity between the object 12 and the surface 10. This deflection of the probe 14 is monitored by the AFM instrumentation. The entire surface 10 may be scanned in this manner, with the AFM instrument collecting data on what objects 12 are removed and also collecting data on the degree of deflection of the probe for each removed object 12. In one embodiment, the degree of deflection can later be utilized to determine the binding affinity of the objects 12 removed at each set point force. In alternative embodiments, the binding affinity can be determined as related to the set point force applied.

In the next step of the present invention method, the removed objects 12 may be collected for characterization and further study. The removed objects 12 in the present invention method are suspended in the liquid medium of the flow cell. Collection of molecules and other materials from flow cells are well known to those in the art and may be accomplished by standard methods. The objects 12 collected may be harvested in this manner for characterization and further study. In alternative embodiments, the objects 12 still bound to the surface 10 may also be harvested for characterization and study. In one alternative embodiment, where deposition domains contain known material at known locations, scanning the surface 10 again to locate where the objects 12 have been removed can tell the user what materials have a relatively high and relatively low binding affinity without having to collect the objects 12 for characterization.

In the next step of the present embodiment, the AFM is again utilized to locate those objects that remain on the surface. As may be appreciated, if the set point was set relatively high compared to the binding affinity of the selected objects 12 to the surface 10, the applied force may have removed all of the objects. Likewise, if the set point was set relatively low, then the applied force may have removed only a few, or none, of the objects 12 on the surface 10. Once the location of the remaining objects 12 is determined, the set point is increased by some pre-determined amount so that the probe 14 and the tip 16 will exert a greater force on the objects 12 during the next scan.

As will be recognized by those skilled in the art, the cycle of locating the objects 12, applying a force on the objects 12, and then harvesting the objects 12 displaced into the solution, may be repeated a number of times. Depending on the variety of objects 12 placed on the surface 10, the range of different forces required to remove them from the surface 10 may be small or large.

If the incremental increase in force is particularly small, then the binding affinity between the object 12 and the surface 10 of those objects 12 removed during each run can be approximated from the known set point force. In one alternative embodiment, the degree of deflection of the probe can be utilized (as described below) to separately calculate the binding affinity. Where the incremental force is increased a larger amount, utilizing the degree of deflection of the probe may be the most accurate method of determining the relative and absolute binding affinity between the object 12 and the surface 10. When smaller incremental set point forces are applied to the objects 12, the binding affinity may be correlated to the set point force applied to determine a hierarchy of the different binding affinities.

As may be appreciated, the present invention method is particularly useful for studying the binding affinity between a first object 12 and a second object. The first object 12 may be bound to the surface and the second object 12 may be bound thereto. Separating the second object 12 from the first object 12 may enable the user to characterize the binding affinity between the two objects 12. Such interactions may include, but are not limited to: complementary and partially complementary nucleic acids, drug candidate molecules and their molecular targets, proteins constituting the partial or complete proteome of an organism or organisms, viruses, bacteriophage, plant and animal cells, as well as materials and systems of all varieties.

The present invention method is particularly advantageous because it does not require the repetitive bench chemistry reactions and the utilization of a sequential series of microtiter plate runs. Furthermore, the present invention is advantageous because various different types of objects 12 can be bound to the same surface, or the same material deposited on the surface, for simultaneous comparison of the various binding affinities.

The Apparatus

A description of the elements of the present invention will now be undertaken in order to more fully explain the present invention.

The object 12 may be placed, deposited, connected, or adsorped on or to the surface in any manner known to those skilled in the art, including, but not limited to, mechanical deposition, in situ chemical synthesis, "ink jet" printing, or other deposition methods, such as adsorption from solution, biomolecular recognition, and non-covalent or covalent chemical attachment. The object 12 may be a molecule, a biomolecule such as a protein or a cell, an inorganic molecule, or some other particle, such as a phage particle, that is of interest for study. In addition, further objects 12 for study may be placed on the surface 10 without changing the nature and scope of the present invention.

Alternative embodiment binding affinities may include:

Spontaneous adsorption In this method a material may be adsorbed from solution directly to a surface. The process of attachment is not necessarily well defined, but it is uniform for all like objects being adsorbed. The attachment mechanism may include electrostatic, hydrophobic or other components.

Defined electrostatic interactions In this method a surface with a defined electrostatic nature is created. For example, poly-L-lysine can be adsorbed to a surface, generating a surface with a relatively uniform distribution of positive charges. Then, a material is adsorbed to the poly-L-lysine coated surface via interactions between negatively charged moieties on the material and the positively charged surface. Variations in the surrounding solution, which may contain electrolytes and buffers of various pH, can effect the tenacity of binding of materials to the surface.

Defined hydrophobic interactions In this method a defined hydrophobic surface is created and bound to materials. In one example, the hydrophobic surface is prepared by coating a substrate with gold, followed by treatment with an alkanethiolate with a terminal (distal) methyl group. This surface is then used as the deposition substrate for materials. Those materials with strong hydrophobic domains will bind more tightly to the distal methyl groups than will those with less hydrophobic domains.

Covalent In some cases it may be desirable to distinguish between materials that are covalently bound and those that are non-covalently bound to a surface. In that case, a defined chemical coupling chemistry may be employed.

Electrodeposition In this method a material is drawn to a surface by forces generated through an electric field. Either an asymmetric AC or a DC field may be used, creating a dielectrophoretic or electrophoretic environment, respectively. The materials may be attached to the surface by a spontaneous mechanism, as described above, or the attachment may involve a more defined coupling method. In one case, a reduction-oxidation (redox) reaction may occur between the material being deposited and the surface, resulting is a covalent coupling between the surfaces. For this method, the surface is usually conductive and coupled to an electrode. A second electrode is also present in the system to complete the circuit and generate the electric field.

Chemical crosslinking In this method a surface is prepared by standard methods which has a defined chemical character. For example, a glass surface may be coated with a silane derivative that has a free distal amino group. After lateral crosslinking of the silane surface to stabilize it, a material may be added to the surface and coupled through a number of chemical reactions involving primary amines, which are well know in the art.

Any of the above binding interactions may be characterized utilizing the present invention without changing the nature and scope of the present invention.

As previously mentioned, the surface 10 of the present embodiment is made of glass over which a sputtered gold layer has been deposited. Such a surface is particularly useful because a glass cover that is covered with a sputtered gold layer are well known in the art and easily obtained (or made). Glass slides with a sputtered gold layer are particularly useful because of their smooth and consistent surface 10 properties. Sputtering gold may produce an extremely smooth surface upon which a variety of chemistry and molecular binding may be performed. A gold surface may be advantageous because of the above reasons, though other coverings or surfaces without coverings may be utilized without changing the nature and scope of the present invention.

In other embodiments, the gold may be sputtered onto smooth silicon, quartz or a similar flat surface, such as mica, modified Si, (poly) tetrafluoroethylene, functionalized silanes, polystyrene, polycarbonate, polypropylene, or combinations thereof. The smoothness required of the underlying substrate is a function of the sensitivity requirement of a particular test. Those binding affinity assays that utilize smaller objects may require a more uniform surface to achieve satisfactory results. A surface 10 which can accept and bind tenaciously to the object 12 may also be desired depending on the object 12 and the binding affinity under study.

The object 12 residing on the surface 10 may be limited to one object 12 bound to the surface 10. In further embodiments, the surface 10 may comprise one, a few, or a hundred or more objects bound to the surface. Each object may be bound in a known area or an in an unknown area which is then determined by utilizing a standard AFM scan. Furthermore, the objects 12 may be one particular type of molecule or particle, or may be a variety of molecules, biomolecules, or particles that are being studied simultaneously to determine their relative binding affinity.

As may be appreciated by those skilled in the art the probe 14 and the tip 16 may comprise one unit. The AFM controls the movement of the probe 14 and the tip 16 and therefore exerts the force on the objects 12. An unmodified AFM probe has a sharp point with a radius of curvature that may be between 5 and 40 nm. The method herein uses a microfabricated probe with an apical radius on the order of 10–50 nm. In the present invention method, the AFM is utilized to move the probe because it is a standard available instrument that has the microfine control necessary to achieve the desired results. One such instrument particularly suited for use in the present method is a Dimension 3100 available from Digital Instruments, Inc., Santa Barbara, Calif. In further embodiments other control devices, including other types of scanning probe microscopes, may be used to control the probe and the tip.

Figure 2A:
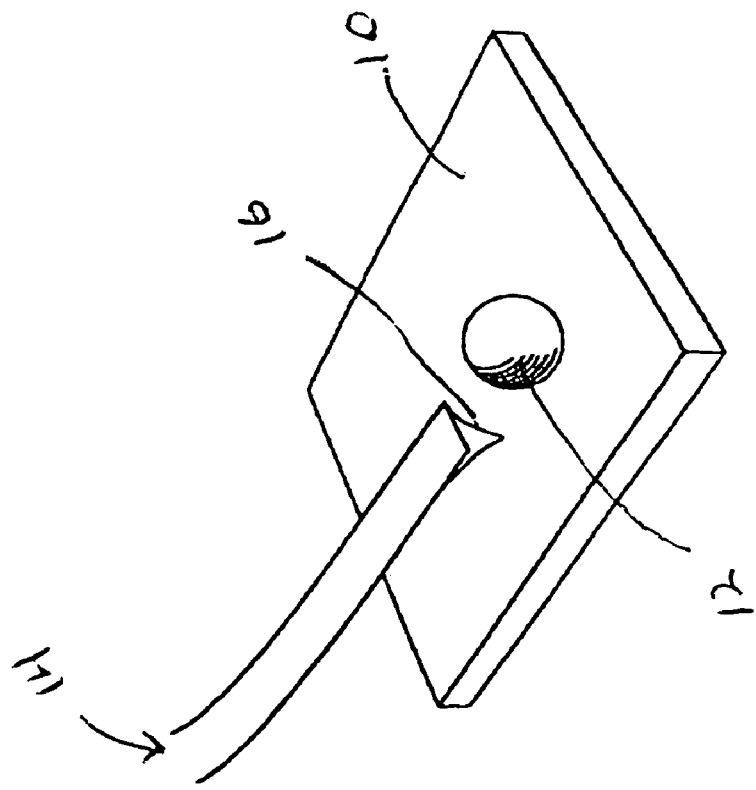
FIG. 2a illustrates an elevational view of a probe approaching an object on a surface.

When the probe 14 contacts an object 12 directly, a vertical force will exist between the object and the probe 14 such that the force is trying to push the object in one direction. As may be appreciated, and as illustrated in FIGS. 2a and 2b, the tip 16 may make an off center contact in such a manner that causes twisting of the probe 14. In such situations, the probe 14 is subject to both a vertical and torsional force interaction with the object 12. The object 12 is then also subject to a vertical force and a torsional force. This may result in a vertical displacement of the tip 16 and probe 14, as shown in FIG. 1a, but also a torsional twisting of the probe 16 as illustrated in FIG. 2b. The AFM instrumentation, however, is able to simultaneously read both the torsional and vertical forces present as indicated by the bending and the twisting of the probe 14. Both the vertical and torsional force may then be utilized to determine the amount of force being exerted on the surface 10 or the object 12.

Since the spring constant of the probe 14 is known, the force exerted on the object 12, up to and including the point at which the object 12 is removed from the surface 10, can be readily calculated by using Hook's law: $F=kX$, where $F$ is the force, $k$ is the spring constant, and $X$ is the displacement distance.

The degree of loading required to displace the object 12 from the surface 10, or some deposition material bound to the surface 10, can be directly correlated with the binding strength the object 12 has with the surface 10. Torsion of the probe 14 and frictional interactions between the tip and the surface 10 can make quantitative measurements complex, but relative force measurements are easily obtained.

In the present embodiment, the applied vertical force is measured by monitoring the deflection of the AFM probe up to and including the point at which the object 12 is removed. As may be appreciated, the lag time between the increasing force being applied to the object 12, and the measurement taken by the probe, may result in some amount of force being exerted in an object that is not directly measured. This gap, however, may be calculated with the AFM instrumentation or with a computer.

EXAMPLE 1

Molecular Force Panning

In this example, the present invention is used to selectively remove an antibody from an antigen that is bound to the surface 10. The binding affinity between the antibody and the antigen is then determined. This example shows how the present invention may be utilized to measure the binding affinity between a deposited rabbit IgG and an anti rabbit IgG.

The surface in this example consists of a glass slide covered by a sputtered gold layer. The rabbit IgG is bound to the gold surface by non-specific binding interactions. The surface is then inserted into an AFM flow cell containing an aqueous imaging environment; in this case a saline-phosphate buffered solution. The buffered solution is a pH 7.5 20 millimolar PBS solution that is trapped between the piezo of the AFM and the surface on which the rabbit IgG has been placed. In the present embodiment the rabbit IgG is placed randomly on the surface and the surface is scanned to determine the locations of the antigens on the surface. As may be appreciated, the antigens may be placed in known locations on the surface utilizing a number of methods and so may therefore reside in domains of known location and size. In still further embodiments, the antibody/antigen complexes may be at random and unknown locations on the surface. Determination of the binding affinities may still be easily accomplished utilizing the present invention. Various deposition techniques, such as dipping the surface in a solution containing the antigen may also be utilized.

Addition of the antibody is accomplished by micropipetting 1 microliter of 0.1 mg/mL PBS into the flow cell. The surface is then scanned using a standard AFM scan and probe to determine the location of the antigen/antibody interactions. After increasing the set point level of the AFM, a subsequent scan is taken. Careful monitoring of the deflection of the probe shows where contact with the antigen/antibody complexes occur. Incremental increases of the set point are then accomplished, resulting in the removal of the antibody from the antigen within a fairly narrow range of applied force. The removal of the antibody within a narrow range is expected because of the uniform identity of the complexes formed. Performing standard AFM scans between each increase in the set point force helps to indicate when the antigen/antibody complexes are separated. The force value that correlates to the force required to break apart the antigen/antibody can then be utilized to determine their relative binding affinity. The binding affinity can also be calculated for the deflection of the probe as monitored by the AFM instrumentation when the antigen and antibody complex is removed.

As may be appreciated, the above example can be repeated with a number of different antigens to determine their relative binding affinity to a corresponding antibody. In further embodiments, various antibodies or antigens can be run simultaneously to determine the relative binding affinity of each. Which antibodies are torn off at various force levels can be determined by collecting the aqueous imaging solution and running characterization tests to determine the antibody removed at that force set point.

In further embodiments, the antigen/antibody complexes can be bonded to the surface to insure that the whole complex is not removed during the increased set point scans.

EXAMPLE 2

Force Panning for Affinity Based Selection of Phage and Virus Interactions

As is illustrated in FIG. 3a–c, force panning may alternatively be used to selectively remove weakly bound virus or phage particles from a surface to allow for the harvesting and identification of those particles with a high binding affinity to the surface. Phage display is a method known in the art for displaying a large ensemble of potentially desirable recombinant proteins on the surface of a phage particle. Phage are engineered so that they produce a specific protein on the surface. Very large combinatorial libraries of proteins can be displayed on the surface of a phage and selected by some screening mechanism. Once selected, the desired phage can be propagated and the molecule with the desired properties can be purified and identified. This is a powerful method for analyzing large libraries of recombinant biomolecules.

Once a phage population is constructed, it may be sorted to find those few phage that are displaying the molecule of interest. In the past, this was accomplished by the repetitive binding and washing of phage from microtiter dishes coated with a molecule to which the displayed molecule binds. Force panning overcomes a number of limitations of this tedious process.

In the present invention example, an intracellular matrix protein that binds to fibronectin is utilized. The present example illustrates how various proteins that bind to fibronectin may be differentiated by binding affinity.

The phage are made and purified by standard methods. The surface utilized in this example is again glass covered with sputtered gold. The fibronectin are allowed to bind to the surface by spontaneous and non-specific binding interactions and the phage are complexed thereto. As may be appreciated, the fibronectin may, in alternative embodiments, be covalently or otherwise fixedly bonded to the surface or some deposition material deposited on the surface.

Excess phage not bound to fibronectin may be washed from the gold surface. The surface with the fibronectin and phage complexes are then placed in the AFM instrument and imaged at a low applied force to determine the location of the bound complexes. The set point is then incrementally increased to increase the force applied to the fibronectin/phage complex. The loosely bound phage particles are subsequently removed from the surface by each applied set point force and diffuse away in the overlying solution. The solution utilized is a binding buffer containing Tris buffer, pH 7.2, NaCl (100 mM). Other solutions that contain this and other buffers may be utilized as desired. The solution in which the process is carried out can be cycled or flowed through the imaging chamber to increase the removal of phage particles that have been removed from the surface by the force panning process. The phage removed at each incrementally increased force may be collected and identified for further study. The force may be increased until all of the phage are removed or may be stopped after a certain set point is reached. The phage remaining on the surface after the last applied force may also be collected for further study.

Several methods may be used to collect the phage that remain bound to the surface following force panning. One way may be to wash the surface with a high salt (e.g. 500 mM NaCl) solution containing, if desired, a surfactant such as Tween-80 to facilitate removal of the remaining phage into solution. This can then be used as the source of the phage particles for propagation and analysis of those with the greatest binding affinities.

An alternative approach for collecting the phage is to use an AFM probe that has been coated with an adherent layer (e.g., fibronectin protein in this case) which can collect the phage particle(s) from the surface for subsequent recovery. This approach requires fine tuning of the relative binding forces to optimize transfer of phage from the surface to the probe.

EXAMPLE 3

Force Panning for Affinity Based Selection of Cell-Surface Interactions

In another example, force panning may be used to assay the tenacity with which cells bind to a variety of surfaces and materials deposited on the surface. The adhesive force between cells and surfaces is a critical parameter in various physiological functions. If, for example, blood cells bind too tightly to arterial walls, blockage of blood flow can occur, resulting in physiological dysfunction or even death. The present invention method may also be utilized to help characterize the amount of adhesive force between different types of cells and various surfaces. Such a method allows for the characterization of surfaces with low or high adhesive properties to the cell of interest. (In this case, cells may not be bound to the surface in a traditional molecular interaction sense, but may adhere to the surface through non-specific interactions). This technique may be useful to determine the likelihood of materials used in biological systems adhering cells and other biological materials thereto.

Figure 4B:
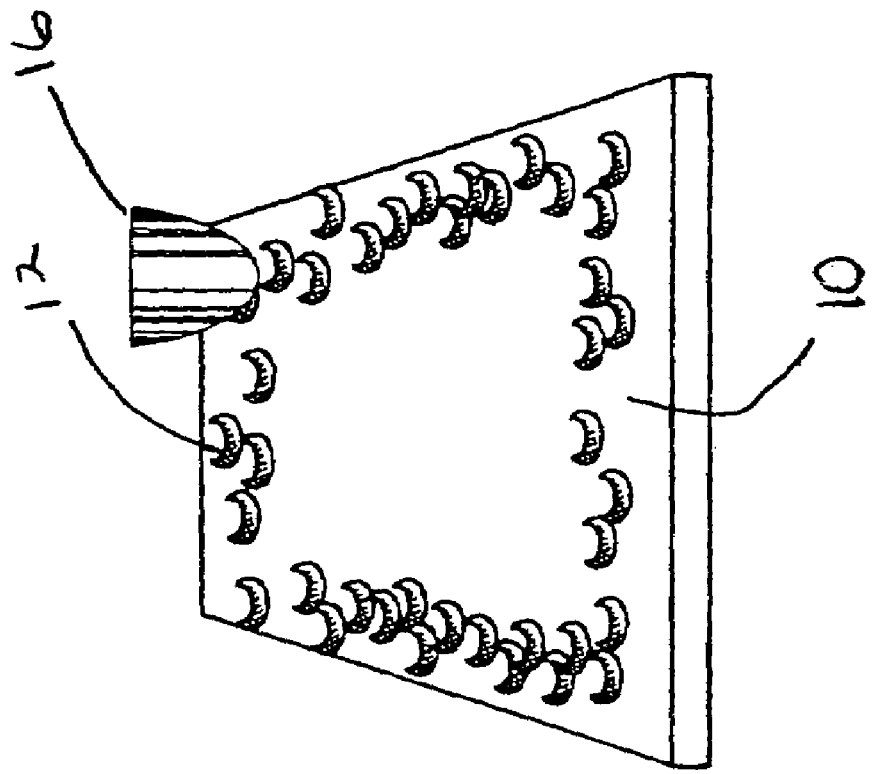
FIG. 4b is a front perspective view of the cells of FIG. 4a after scanning with a probe wherein a number of the cells are removed.
Figure 4A:
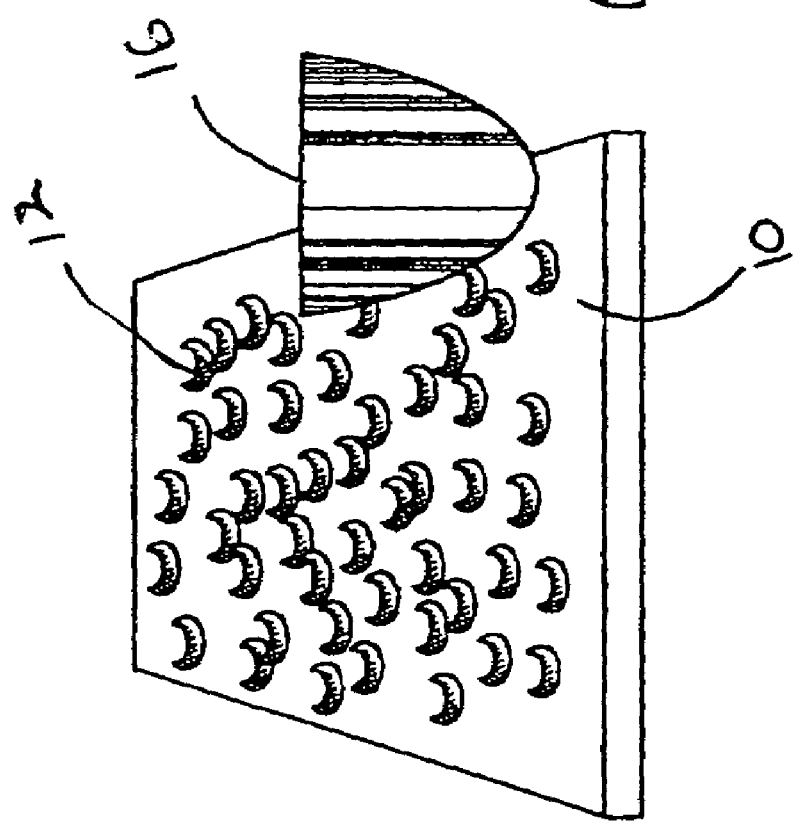
FIG. 4a is a front perspective view of a distribution of bound cells on a surface.
Figure 5B:
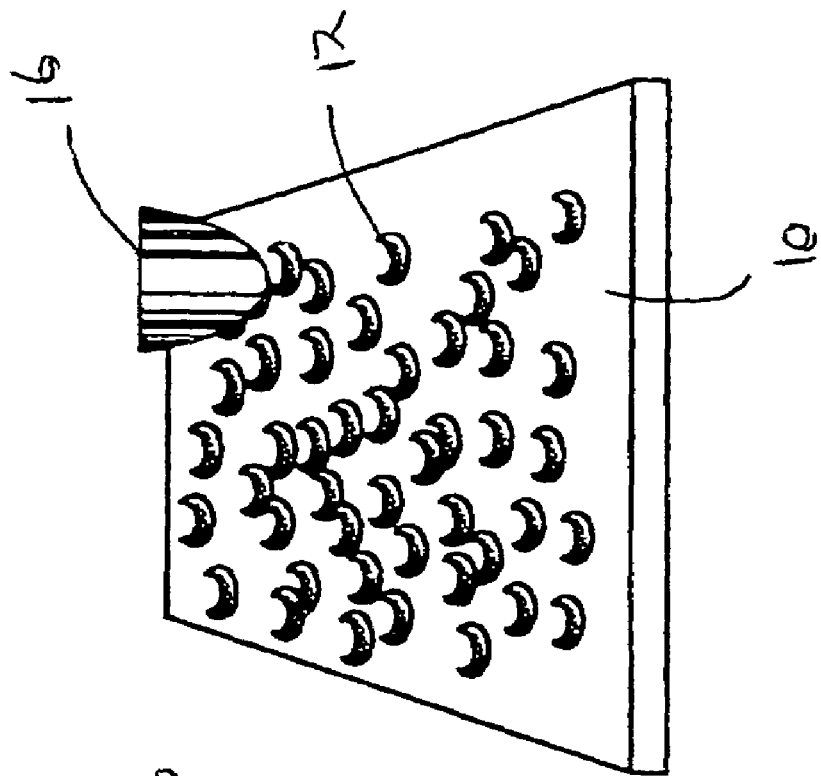
FIG. 5b is a front perspective view of the cells of FIG. 5a after scanning with a probe wherein few cells are removed.
Figure 5A:
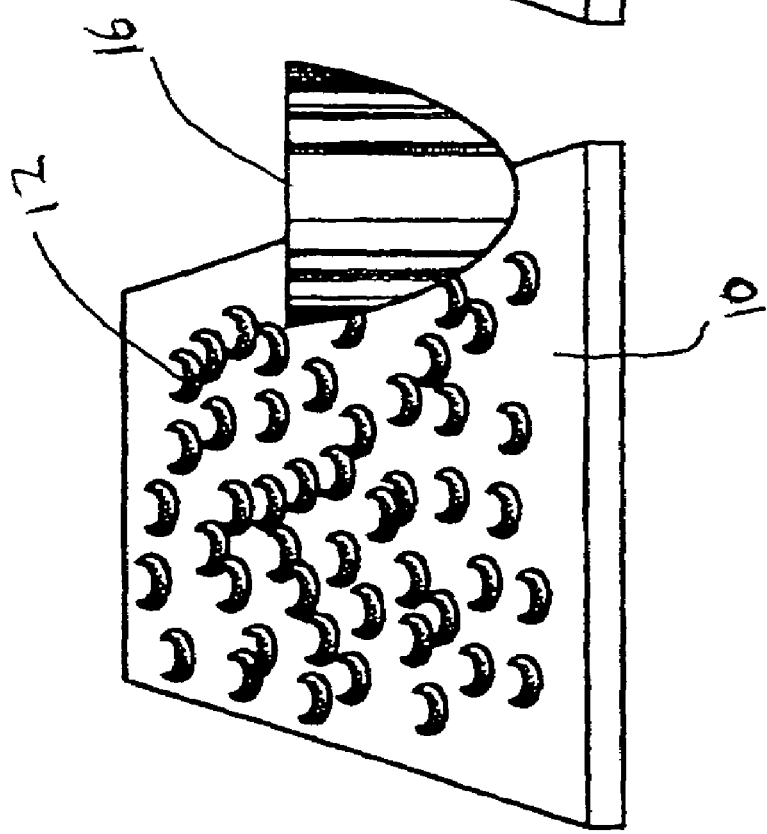
FIG. 5a is a front perspective view of a distribution of bound cells on a surface.

In this example red blood cells are allowed to bind to glass coated with a first synthetic polymer (polymer 1) (FIG. 4a). After binding, the cells are subjected the present invention method to determine the binding affinity. The scans are carried out in a physiological solution (e.g., PBS) and the force required to remove cells from the surface is noted. Then the same cell type is allowed to bind to a surface coated with a second polymer (polymer 2) and the process repeated (FIG. 5a). By comparing the forces necessary to remove the cells from each surface, the polymers can be compared with respect to their ability to bind, or not to bind, red blood cells. The adhesive measurement can be based upon the torsion and vertical force applied by the probe. Quantitative measurements can be obtained by calculating the force used to displace the cells.

In an alternative embodiment, the various polymers can be "printed" onto a surface by contact or inkjet printing. This surface is then incubated with red blood cells and all of the polymers under scrutiny are tested simultaneously in a single force panning experiment.

In FIG. 4b, the cells bind to the surface with a force lower than that generated by the scanning process. Because of the low cell binding force, the majority of the cells are displaced from the surface during scanning. In FIG. 5b, cells bind to the surface with a force greater than that generated by the scanning process. The cells are not displaced by the AFM scanning across the surface that applies the set point force. Variations of this process allow the user to acquire quantitative information regarding the strength of cell/surface binding.

In one alternative embodiment, a specialized AFM probe is used to minimize cell damage. The specialized probe can be made "blunt" by bonding a microparticle to the end of an AFM probe. Binding of a microparticle to the end of the probe may be further described in co-pending U.S. application Ser. No. 09/574,519. The blunted probe has a reduced chance of slicing into the cells being analyzed, acting more like a plow to push against the soft cells without rupturing them.

In another alternative embodiment, the cells may be isolated and reproduced in large numbers so that the proteins responsible for the cell-substrate interaction can be identified. In the case of cells containing recombinant proteins, this process can be considered analogous to the phage display process in that the cells can be used to amplify cell surface proteins with certain desirable characteristics.

In yet another alternative embodiment the force applied to each object may remain constant to determine the effect of a repetitious constant force being applied to the object. As may be appreciated, other studies may also be conducted to analyze the binding affinity of the object to the surface, or the material deposited on the surface.

The information and examples described herein are for illustrative purposes and are not meant to exclude any derivations or alternative methods that are within the conceptual context of the invention. It is contemplated that various deviations can be made to this embodiment without deviating from the scope of the present invention. Accordingly, it is intended that the scope of the present invention be dictated by the appended claims rather than by the foregoing description of this embodiment.

The invention claimed is:

1. A method for determining a binding affinity between an object and one or more materials using a scanning probe microscope comprising:
   (a) obtaining a surface, the surface further comprising one or more materials deposited thereon;
   (b) affixing at least one object to the one or more materials deposited on the surface;
   (c) applying a force with a tip of the scanning probe microscope to a first object to remove the first object from a first material, wherein the first object is displaced from the first material and the tip; and
   (d) calculating the binding affinity between the first object and the first material from the force applied to remove the object from the first material.

2. The method of claim 1, further comprising monitoring the force required to remove the first object from the material.

3. The method of claim 1, further comprising scanning the surface of step (b) to locate a first object.

4. The method of claim 3, wherein scanning the surface and applying the force is performed in a liquid medium.

5. The method of claim 1, further comprising collecting the displaced first object.

6. The method of claim 1, wherein the first object and first material of step (d) are selected from the group of pairs of substances consisting of: a first protein and a second protein; a first nucleic acid and a second nucleic acid; an antibody and an antigen; a receptor and a ligand; a drug candidate molecule and its molecular target; drugs and drug inhibitors; a first cell and a second cell; a first virus and a second virus; a cell and a substrate; and a virus and a substrate.

7. A method for separating objects based on relative binding affinities using a scanning probe microscope comprising:
   (a) depositing at least one material on a surface;
   (b) affixing a plurality of objects tote at least one material deposited on the surface; and
   (c) applying a first force to the surface with a tip of the scanning probe microscope such tat a first object is removed from a first material deposited on the surface, wherein the first object is displaced from the first material and the tip, and wherein a second object is retained on the first material or on a second material deposited on the surface.

8. The method of claim 7, further comprising scanning the surface of step (c) to locate a first object.

9. The method of claim 7, further comprising collecting the removed first object of step (c).

10. The method of claim 7, further comprising the steps of:
    (d) applying a second greater force to the surface with the scanning probe microscope such that the second object is removed from the first or second material deposited on the surface.

11. The method of claim 10, further comprising collecting the removed second object of step (d).

12. The method of claim 10, further comprising:
    (e) calculating the relative binding affinities of the first object removed in step (c) and the second object removed in step (d).

13. The method of claim 7 further comprising:
    (d) applying an incrementally increased force with the scanning probe microscope to a second object to remove the second object from the first or second material deposited on the surface.

14. The method of claim 13, further comprising collecting the removed second object of step (d).

* * * * *